US008480646B2

(12) United States Patent
Nord et al.

(10) Patent No.: US 8,480,646 B2
(45) Date of Patent: Jul. 9, 2013

(54) MEDICAL DEVICE CONNECTOR

(75) Inventors: Lars Nord, Göteborg (SE); Alexander Cederschiold, Göteborg (SE)

(73) Assignee: Carmel Pharma AB, Goteborg (SE)

( * ) Notice: Subject to any disclaimer, the term of this patent is extended or adjusted under 35 U.S.C. 154(b) by 687 days.

(21) Appl. No.: 12/623,042

(22) Filed: Nov. 20, 2009

(65) Prior Publication Data

US 2011/0125128 A1 May 26, 2011

(51) Int. Cl.
*A61B 19/00* (2006.01)
*A61M 5/32* (2006.01)

(52) U.S. Cl.
USPC ............ 604/414; 604/403; 604/411; 604/415

(58) Field of Classification Search
USPC ................................. 604/403, 411, 414, 415
See application file for complete search history.

(56) References Cited

U.S. PATENT DOCUMENTS

| | | | |
|---|---|---|---|
| 1,844,342 | A | 2/1932 | Berman |
| 2,010,417 | A | 8/1935 | Schwab |
| 2,697,438 | A | 12/1954 | Hickey |
| 2,717,599 | A | 9/1955 | Huber |
| 3,064,651 | A | 11/1962 | Henderson |
| 3,071,135 | A | 1/1963 | Baldwin et al. |
| 3,308,822 | A | 3/1967 | DeLuca |
| 3,316,908 | A | 5/1967 | Burke |
| 3,340,671 | A | 9/1967 | Loo |
| 3,390,677 | A | 7/1968 | Razimbaud |
| 3,448,740 | A | 6/1969 | Figge |
| 3,542,240 | A | 11/1970 | Solowey |
| 3,783,895 | A | 1/1974 | Weichselbaum |
| 3,788,320 | A | 1/1974 | Dye |
| 3,822,700 | A | 7/1974 | Pennington |

(Continued)

FOREIGN PATENT DOCUMENTS

| | | |
|---|---|---|
| AU | 200112863 | 5/2003 |
| DE | 1005685 | 4/1957 |

(Continued)

OTHER PUBLICATIONS

Taiwan Search Report for Taiwan Patent Application 092106323 dated Mar. 21, 2003 (4 pages).

(Continued)

*Primary Examiner* — Tatyana Zalukaeva
*Assistant Examiner* — Ginger T Chapman
(74) *Attorney, Agent, or Firm* — Servilla Whitney LLC

(57) ABSTRACT

The present invention relates to a first medical device (1, 100) configured to permit connection to a second medical device (3). The medical device (1, 100, 200) comprises a guiding track (12) for receiving a lock protrusion (4). The guiding track (12) comprises a surface (16) having a lock edge (15) extending between a first and a second level (H1, H2). The lock edge (15) extends in a smooth curvature between the first and the second level (H1, H2), the curvature of which is a function of at least of radius (Ra). The medical device (1, 100) may comprise a neck element (11) with at least one guiding track (12) for receiving a lock protrusion (4) of a second medical device (3) or optionally the medical device may comprise a sleeve member (202) which comprises the guiding track (12). The present invention provide for a connection site which enables a smooth lock but especially a smooth unlock motion of the second medical device being connected.

16 Claims, 8 Drawing Sheets

U.S. PATENT DOCUMENTS

| | | | |
|---|---|---|---|
| 3,938,520 A | 2/1976 | Scislowicz et al. | |
| 3,976,073 A | 8/1976 | Quick et al. | |
| 4,096,860 A | 6/1978 | McLaughlin | |
| 4,296,786 A | 10/1981 | Brignola | |
| D270,568 S | 9/1983 | Armstrong | |
| 4,490,139 A | 12/1984 | Huizenga et al. | |
| 4,516,967 A | 5/1985 | Kopfer | |
| 4,564,054 A | 1/1986 | Gustavsson | |
| 4,573,967 A | 3/1986 | Hargrove et al. | |
| 4,576,211 A | 3/1986 | Valentini et al. | |
| 4,581,016 A | 4/1986 | Gettig | |
| 4,582,223 A | 4/1986 | Kobe | |
| 4,588,403 A | 5/1986 | Weiss et al. | |
| 4,600,040 A | 7/1986 | Naslund | |
| 4,623,343 A | 11/1986 | Thompson | |
| 4,629,455 A | 12/1986 | Kanno | |
| 4,632,673 A | 12/1986 | Tiitola et al. | |
| 4,636,204 A | 1/1987 | Christopherson et al. | |
| 4,673,010 A * | 6/1987 | Prufer et al. | 141/382 |
| 4,673,400 A | 6/1987 | Martin | |
| 4,673,404 A | 6/1987 | Gustavsson | |
| 4,737,150 A | 4/1988 | Baeumle et al. | |
| 4,752,287 A | 6/1988 | Kurtz et al. | |
| 4,759,756 A | 7/1988 | Forman et al. | |
| 4,768,568 A | 9/1988 | Fournier et al. | |
| 4,792,329 A | 12/1988 | Schreuder | |
| 4,804,015 A | 2/1989 | Albinsson | |
| 4,822,340 A | 4/1989 | Kamstra | |
| 4,826,492 A | 5/1989 | Magasi | |
| 4,834,717 A | 5/1989 | Haber et al. | |
| 4,842,585 A | 6/1989 | Witt | |
| 4,850,978 A | 7/1989 | Dudar et al. | |
| 4,864,717 A | 9/1989 | Baus, Jr. | |
| 4,872,494 A | 10/1989 | Coccia | |
| 4,878,897 A | 11/1989 | Katzin | |
| 4,889,529 A | 12/1989 | Haindl | |
| 4,898,209 A | 2/1990 | Zbed | |
| 4,909,290 A | 3/1990 | Coccia | |
| 4,932,937 A | 6/1990 | Gustavsson et al. | |
| 4,944,736 A | 7/1990 | Holtz | |
| 4,964,855 A | 10/1990 | Todd et al. | |
| 4,982,769 A | 1/1991 | Fournier et al. | |
| 4,994,048 A | 2/1991 | Metzger | |
| 4,997,083 A | 3/1991 | Loretti et al. | |
| 5,017,186 A | 5/1991 | Arnold | |
| 5,041,105 A | 8/1991 | D'Alo et al. | |
| 5,061,264 A | 10/1991 | Scarrow | |
| 5,071,413 A | 12/1991 | Utterberg | |
| 5,122,116 A | 6/1992 | Kriesel et al. | |
| 5,122,123 A | 6/1992 | Vaillancourt | |
| 5,137,524 A | 8/1992 | Lynn et al. | |
| 5,139,483 A | 8/1992 | Ryan | |
| 5,158,554 A | 10/1992 | Jepson et al. | |
| 5,176,673 A | 1/1993 | Marrucchi | |
| 5,199,947 A | 4/1993 | Lopez et al. | |
| 5,201,725 A | 4/1993 | Kling | |
| 5,207,658 A | 5/1993 | Rosen et al. | |
| 5,232,109 A | 8/1993 | Tirrell et al. | |
| 5,254,097 A | 10/1993 | Schock et al. | |
| 5,279,576 A | 1/1994 | Loo et al. | |
| 5,279,583 A | 1/1994 | Shober, Jr. et al. | |
| 5,279,605 A | 1/1994 | Karrasch et al. | |
| 5,308,347 A | 5/1994 | Sunago et al. | |
| 5,312,366 A | 5/1994 | Vaillancourt | |
| 5,328,480 A | 7/1994 | Melker et al. | |
| 5,334,163 A | 8/1994 | Sinnett | |
| 5,356,406 A | 10/1994 | Schraga | |
| 5,385,545 A | 1/1995 | Kriesel et al. | |
| 5,385,547 A | 1/1995 | Wong et al. | |
| 5,389,085 A | 2/1995 | D'Alessio et al. | |
| 5,405,326 A | 4/1995 | Haber et al. | |
| 5,445,630 A | 8/1995 | Richmond | |
| 5,447,501 A | 9/1995 | Karlsson et al. | |
| 5,456,675 A | 10/1995 | Wolbring et al. | |
| 5,470,522 A | 11/1995 | Thome et al. | |
| 5,478,328 A | 12/1995 | Silverman et al. | |
| 5,478,337 A | 12/1995 | Okamoto et al. | |
| 5,492,531 A | 2/1996 | Post et al. | |
| 5,514,117 A | 5/1996 | Lynn | |
| 5,515,871 A | 5/1996 | Bittner et al. | |
| 5,536,259 A | 7/1996 | Utterberg | |
| 5,575,780 A | 11/1996 | Saito | |
| 5,593,028 A | 1/1997 | Haber et al. | |
| 5,613,954 A | 3/1997 | Nelson et al. | |
| 5,632,735 A | 5/1997 | Wyatt et al. | |
| 5,647,845 A | 7/1997 | Haber et al. | |
| 5,685,866 A | 11/1997 | Lopez | |
| 5,752,942 A | 5/1998 | Doyle et al. | |
| 5,766,147 A | 6/1998 | Sancoff et al. | |
| 5,766,211 A | 6/1998 | Wood et al. | |
| 5,782,872 A | 7/1998 | Muller | |
| 5,795,336 A | 8/1998 | Romano et al. | |
| 5,817,083 A | 10/1998 | Shemesh et al. | |
| 5,820,609 A | 10/1998 | Saito | |
| 5,827,262 A | 10/1998 | Neftel et al. | |
| 5,837,262 A | 11/1998 | Golubev et al. | |
| 5,875,931 A | 3/1999 | Py | |
| 5,879,345 A | 3/1999 | Aneas | |
| 5,897,526 A | 4/1999 | Vaillancourt | |
| 5,934,510 A | 8/1999 | Anderson | |
| 5,984,899 A | 11/1999 | D'Alessio et al. | |
| 6,063,068 A | 5/2000 | Fowles et al. | |
| D427,308 S | 6/2000 | Zinger | |
| 6,070,623 A | 6/2000 | Aneas | |
| 6,071,270 A | 6/2000 | Fowles et al. | |
| 6,090,091 A | 7/2000 | Fowles et al. | |
| 6,113,068 A | 9/2000 | Ryan | |
| 6,113,583 A | 9/2000 | Fowles et al. | |
| 6,142,446 A | 11/2000 | Leinsing | |
| 6,146,362 A | 11/2000 | Turnbull et al. | |
| 6,209,738 B1 | 4/2001 | Jansen et al. | |
| 6,221,065 B1 | 4/2001 | Davis | |
| 6,245,056 B1 | 6/2001 | Walker et al. | |
| D445,501 S | 7/2001 | Niedospial, Jr. | |
| 6,253,804 B1 | 7/2001 | Safabash | |
| 6,258,078 B1 | 7/2001 | Thilly | |
| 6,387,074 B1 | 5/2002 | Horppu et al. | |
| 6,453,956 B2 | 9/2002 | Safabash | |
| 6,471,674 B1 | 10/2002 | Emig et al. | |
| 6,517,523 B1 | 2/2003 | Kaneko et al. | |
| 6,524,276 B1 * | 2/2003 | Halseth et al. | 604/110 |
| 6,537,263 B1 | 3/2003 | Aneas | |
| 6,547,764 B2 * | 4/2003 | Larsen et al. | 604/192 |
| 6,571,837 B2 | 6/2003 | Jansen et al. | |
| 6,591,876 B2 | 7/2003 | Safabash | |
| 6,644,367 B1 | 11/2003 | Savage et al. | |
| 6,685,692 B2 | 2/2004 | Fathallah | |
| 6,715,520 B2 | 4/2004 | Andreasson et al. | |
| 6,761,286 B2 | 7/2004 | Py et al. | |
| D495,416 S | 8/2004 | Dimeo et al. | |
| 6,786,244 B1 | 9/2004 | Jones | |
| 6,855,129 B2 * | 2/2005 | Jensen et al. | 604/110 |
| D506,256 S | 6/2005 | Miyoshi et al. | |
| 6,960,194 B2 | 11/2005 | Hommann et al. | |
| 7,000,806 B2 | 2/2006 | Py et al. | |
| 7,080,672 B2 | 7/2006 | Fournier et al. | |
| 7,281,947 B2 * | 10/2007 | Pescatore | 439/578 |
| 7,297,140 B2 | 11/2007 | Orlu et al. | |
| D570,477 S | 6/2008 | Gallogly et al. | |
| D572,820 S | 7/2008 | Gallogly et al. | |
| D577,438 S | 9/2008 | Gallogly et al. | |
| D577,822 S | 9/2008 | Gallogly et al. | |
| D582,033 S | 12/2008 | Baxter et al. | |
| 7,521,022 B2 * | 4/2009 | Konrad | 422/550 |
| D605,755 S | 12/2009 | Baxter et al. | |
| 7,703,486 B2 | 4/2010 | Costanzo | |
| D616,984 S | 6/2010 | Gilboa | |
| 7,744,581 B2 | 6/2010 | Wallen et al. | |
| 7,975,753 B2 * | 7/2011 | Lehman et al. | 164/466 |
| 8,052,653 B2 * | 11/2011 | Gratwohl et al. | 604/198 |
| 8,262,013 B2 * | 9/2012 | Shimanuki | 242/532.6 |
| 8,336,587 B2 * | 12/2012 | Rosenquist et al. | 141/384 |
| 2001/0021825 A1 | 9/2001 | Becker et al. | |
| 2001/0025671 A1 | 10/2001 | Safabash | |
| 2002/0002352 A1 | 1/2002 | Becker et al. | |
| 2002/0082586 A1 | 6/2002 | Finley et al. | |
| 2002/0127150 A1 | 9/2002 | Sasso | |

| | | | |
|---|---|---|---|
| 2002/0177819 | A1 | 11/2002 | Barker et al. |
| 2003/0010717 | A1 | 1/2003 | Brugger et al. |
| 2003/0070726 | A1 | 4/2003 | Andreasson et al. |
| 2003/0106610 | A1 | 6/2003 | Roos et al. |
| 2003/0107628 | A1 | 6/2003 | Fowles et al. |
| 2003/0199846 | A1 | 10/2003 | Fowles et al. |
| 2003/0233083 | A1 | 12/2003 | Houwaert et al. |
| 2004/0116858 | A1 | 6/2004 | Heinz et al. |
| 2004/0199139 | A1 | 10/2004 | Fowles et al. |
| 2004/0215147 | A1 | 10/2004 | Wessman et al. |
| 2005/0215977 | A1 | 9/2005 | Uschold |
| 2006/0025747 | A1 | 2/2006 | Sullivan et al. |
| 2006/0106360 | A1 | 5/2006 | Wong |
| 2006/0111667 | A1 | 5/2006 | Matsuura et al. |
| 2006/0157984 | A1 | 7/2006 | Rome et al. |
| 2006/0186045 | A1 | 8/2006 | Jensen et al. |
| 2007/0021725 | A1 | 1/2007 | Villette |
| 2007/0060841 | A1 | 3/2007 | Henshaw |
| 2007/0088313 | A1 | 4/2007 | Zinger et al. |
| 2007/0106244 | A1 | 5/2007 | Mosler et al. |
| 2007/0179441 | A1 | 8/2007 | Chevallier |
| 2007/0270759 | A1 | 11/2007 | Pessin |
| 2007/0270778 | A9 | 11/2007 | Zinger et al. |
| 2008/0045919 | A1 | 2/2008 | Jakob et al. |
| 2008/0103453 | A1 | 5/2008 | Liversidge |
| 2008/0103485 | A1 | 5/2008 | Kruger |
| 2008/0172039 | A1 | 7/2008 | Raines |
| 2008/0223484 | A1 | 9/2008 | Horppu |
| 2008/0287920 | A1 | 11/2008 | Fangrow et al. |
| 2008/0312634 | A1 | 12/2008 | Helmerson et al. |
| 2009/0024093 | A1 | 1/2009 | Laurent et al. |
| 2009/0254042 | A1 | 10/2009 | Gratwohl et al. |
| 2010/0137827 | A1 | 6/2010 | Warren et al. |
| 2010/0204671 | A1 | 8/2010 | Kraushaar et al. |
| 2010/0243099 | A1 | 9/2010 | Yodfat |

FOREIGN PATENT DOCUMENTS

| | | |
|---|---|---|
| DE | 2005519 | 10/1979 |
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| FR | 2884723 | 10/2006 |
| GB | 1579065 | 11/1980 |
| JP | 49-12690 | 5/1972 |
| JP | 288664 | 7/1990 |
| JP | 3030963 | 8/1996 |
| JP | 2000167022 | 6/2000 |
| JP | 2001505092 | 4/2001 |
| JP | 2001293085 | 10/2001 |
| TW | 482670 | 4/2002 |
| WO | WO 84/04672 | 12/1984 |
| WO | WO 84/04673 | 12/1984 |
| WO | WO 90/03536 | 4/1990 |
| WO | WO 98/19724 | 5/1998 |
| WO | WO 99/27886 | 6/1999 |
| WO | WO 99/62578 | 12/1999 |
| WO | WO 00/05292 | 2/2000 |
| WO | WO 00/35517 | 6/2000 |
| WO | WO 01/80928 | 11/2001 |
| WO | WO 02/02048 | 1/2002 |
| WO | WO 02/11794 | 2/2002 |
| WO | WO 02/064077 | 8/2002 |
| WO | WO 02/076540 | 10/2002 |
| WO | WO 2005/074860 | 8/2005 |
| WO | WO 2006/082350 | 8/2006 |
| WO | WO 2006/083333 | 8/2006 |
| WO | WO-2006/103074 | 10/2006 |
| WO | WO-2007/040396 | 4/2007 |
| WO | WO 2008/115102 | 9/2008 |
| WO | WO 2006/138184 | 12/2009 |

OTHER PUBLICATIONS

Japan Application No. 2003-583539, Official Action dated May 1, 2009 (3 pages).
Japan Application No. 2003-577789, Official Action dated Feb. 24, 2009 (4 pages).
International Search Report, PCT/EP2008/067535 dated Oct. 13, 2009 (3 pages).
International Search Report, PCT/EP2008/067522 dated Aug. 12, 2009 (2 pages).
“Translation of DE1005685” , 2012.

* cited by examiner

MEDICAL DEVICE CONNECTOR

TECHNICAL FIELD

The present invention relates to a connection site for a medical device having a neck element with at least one guiding track. The guiding track has a lock edge for cooperative engagement with a lock protrusion of a second medical device.

BACKGROUND OF THE INVENTION

Administration of hazardous medicaments such as cytotoxins and the like has long been a nuisance to the personal which on daily basis administrate the hazardous medicaments. During preparation of medicaments, administration or after treatment, nursing personal is exposed to the risk of contamination from the hazardous medicaments. Such contamination may be in the form of liquid, aerosols, or vapours, medicaments, derived from spillage due to ill handling or just wrong handling of equipments or instruments. Leakage from technical equipment which has been used right is however also a problem, even if leakage occur in very small doses. Due to long exposure to hazardous medicaments nursing personal can still be ill from very small quantities of hazardous medicaments. It is therefore important to minimize leakage and minimize the risk of leakage.

One specific hazardous step is when e.g. nursing personal is transferring a medicament from one fluid container to another; such transfer usually involves the use of a piercing member such as a needle. To protect the nursing personal involved, piercing member protection devices are commonly used. Such devices are arranged to protect the user, not only from contamination but also from accidentally piercing themselves or any other third persons. One example of such piercing member protection device, having a needle, is disclosed in U.S. Pat. No. 4,564,054 (Gustavsson).

Piercing devices, such as the ones described in the U.S. Pat. No. 4,564,054 (Gustavsson) generally requires a mating connector or adaptor to enable assembly with a vial to prevent leakage. To enable a firm connection with e.g. piercing devices, medical device connectors, also referred to as medical device adaptors, has been developed. It has been found that the connection site on medical devices comprising a neck element with guiding tracks having a locking edge to establish a good connection with a medical device is generally not good to use with second connection sites having threads or a engage/disengagement arrangement which operates by a turning motion. As both connection sites use a turning motion to connect or disconnect, such turning motion could accidentally disconnect a medical device to the medical device connector.

SUMMARY OF THE INVENTION

It is the objective of the present invention to remove or reduce the at least one of the above mentioned drawbacks. This is at least partly done by a first medical device comprising a first connection site for connecting a second medical device. The first connection site comprises at least one guiding track. The at least one guiding track is arranged with a surface comprising a locking edge. The locking edge is arranged to cooperate with a lock protrusion on the second medical device. The locking edge extends between a first and a second level. The locking edge further extends as a smooth curvature between the first and the second level, the curvature of which is a function of at least one radius. The present invention provides for easy usage of a medical device connector which can be smoothly connected or disconnected, locked or unlocked. The radius is preferably about 1-10 mm, more preferably 2-8 mm or even more preferably 3-5 mm.

The medical device can be a medical device connector in which the medical device connector comprises a neck element, such as a cylinder like neck element, extending from a base member for receiving parts of said second medical device; the neck element comprises the at least one guiding track. Optionally the medical device can be a piercing member protection device. The guiding track 12 can in an embodiment be arranged on a sleeve member arranged in a telescopically manner with a second sleeve member.

In an embodiment according to the present invention, the distance between the first and the second level is between about 0.2-3.0 mm, preferably between 0.2-1.0 mm.

In an embodiment according to the present invention, the locking edge extends in a smooth curvature between the first and the second level. The curvature of which is a function of one radius, i.e. only one radius.

The guiding track of the neck element usually comprises a vertical section and a horizontal section arranged substantially perpendicular to the vertical section, and the horizontal section can comprise a distal and proximal surface, a first and a second vertical surface. It should be noted however that these two sections can in an embodiment be arranged with an angle of between about 45-135° with respect to each other.

The radius has advantageously a centre of origin positioned at a distance from the second vertical surface of the guiding track. The distance is advantageously adapted to be between about 3-20 mm. The smooth curvature is preferably initiated from a distance of 1-6 mm, preferably between 2-5 mm from the second vertical surface of the guiding track. In the shown embodiment the distance e is about 2.6 mm. This provides enough space for a lock protrusion of a mating medical device while at the same time keeping the lock protrusion snugly fitted in the guiding track.

The medical device connector can be arranged with at least two connection sites, e.g. it may comprise a second connection site for connecting to two medical devices. The second connection site can comprise threads, and in an embodiment be a male or female luer lock coupling.

In an embodiment according to the present invention, the medical device is a piercing member protection device comprising at least one guiding track. The piercing member protection device is preferably telescopically arranged, i.e. having a first member and a second member being telescopically arranged with respect to each other. The telescopically function enables the piercing member to function between two positions in which the piercing member is either exposed or not exposed. The medical device can comprise a barrier member arranged to cooperate with the lock protrusion of the second medical device so as to exert a force component to the second medical device.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description.

BRIEF DESCRIPTION OF THE DRAWINGS

The present invention will de described in greater detail with reference to the accompanying figures in which.

DEFINITION

By the term "medical device" is meant a device used in hospital environments, nursing environments or care taking environments usually by qualified personnel such as doctors, nurses or the like. Such environments generally have high requirements regarding hygiene, personal care, and a strive towards low risk for contaminations. Typical medical devices are needles, syringes, piercing member protection devices, vials, infusion bags, infusion sets, administration systems, adapters, tubes, medical device connectors for connecting or adapting different medical devices to each other, or the like.

DETAILED DESCRIPTION OF PREFERRED EMBODIMENTS

Figure 1:
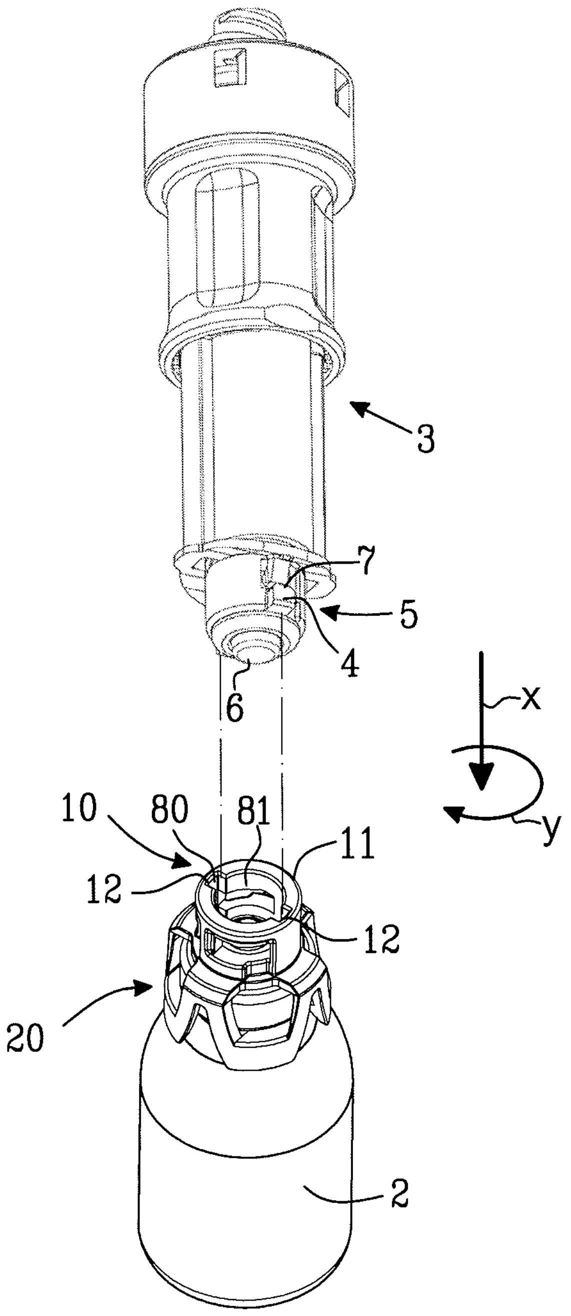
FIG. 1 shows a piercing device in the form of a piercing member protection device with a needle, a medical device connector and a vial; the medical device connector being connected to the vial.

FIG. 1 shows a medical device 1 in the form of a medical device connector 1 for connecting two medical devices. The medical devices can be a vial 2 and a piercing device 3. The piercing device 3 can be a piercing device having a telescopically movable piercing member protection function, as will be outlined below. The medical device connector 1 comprises a first connection site 10 adapted to receive and establish a connection with the piercing device 3 and a second connection site 20 adapted to establish a connection with the vial 2. The second connection site 20 operates by being fitted onto the neck of the vial 2 with a snap on function.

Figure 2A:
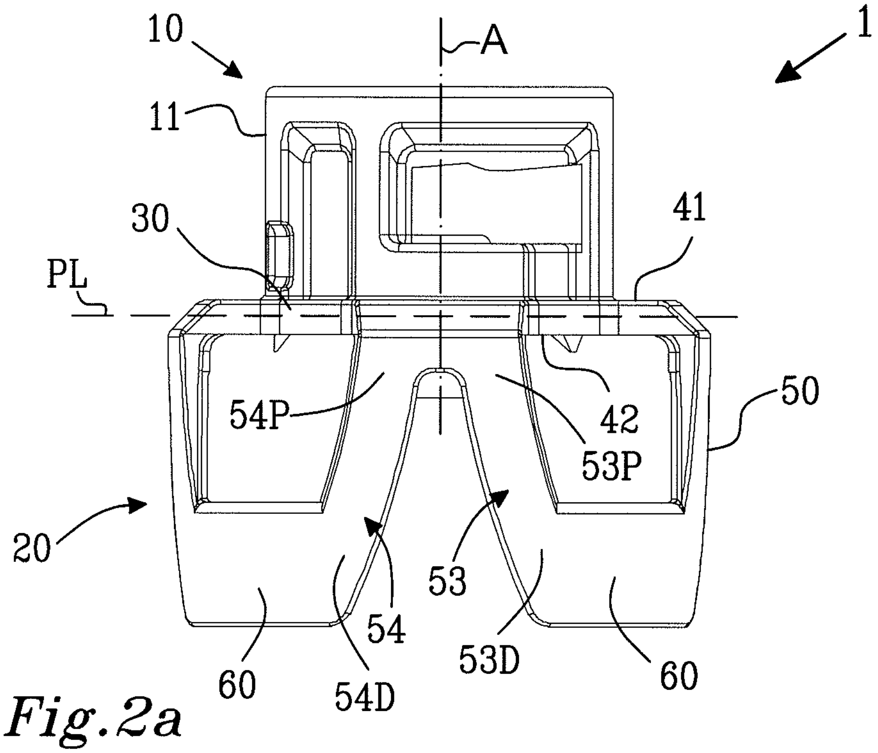
FIGS. 2*a*-2*c* show the medical device connector from FIG. 1 shown in different views.
Figure 2B:
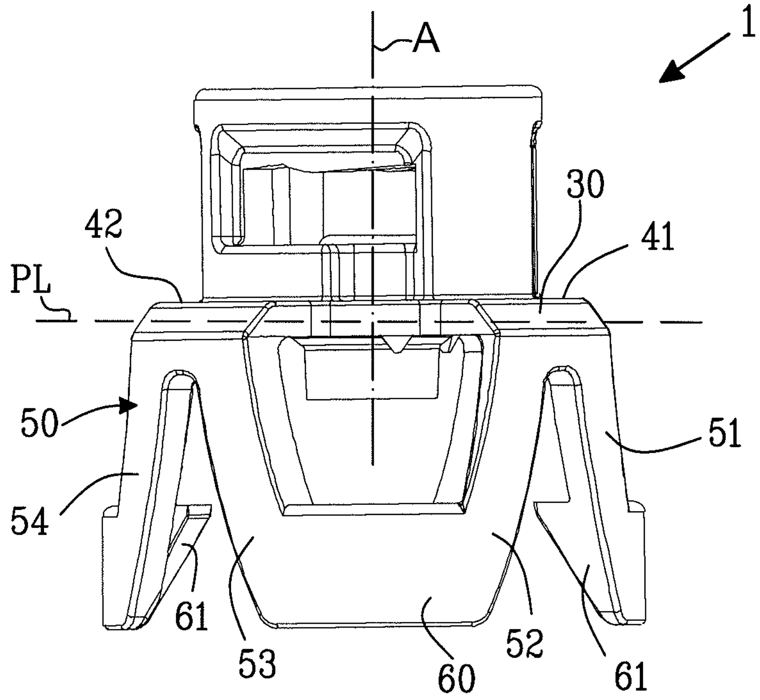
Figure 2C:
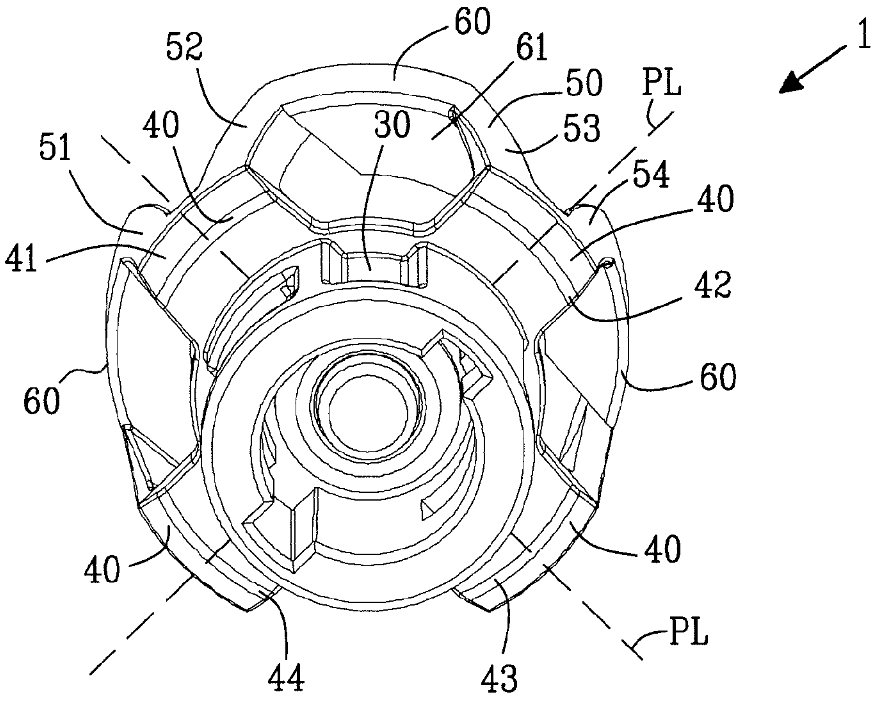

FIGS. 2*a*-2*c* show the medical device connector 1 in different views, the same feature is indicated with the same reference numeral. FIGS. 2*a*-2*c* show the first and the second connection site 10, 20 arranged on a base member 30. The medical device connector 1 has a centre axis A. The base member 30 separates the first and the second site 10, 20 from each other but is formed integrally with the first and the second connection site. The base member 30 has an extension in the plane PL, as indicated in FIGS. 2*a*-2*c*.

A plurality of flanges 40 extends from the base member 30. The embodiment shown in FIGS. 2*a*-2*d* has four symmetrically positioned flanges 40; a first, a second, a third and a forth flange 41, 42, 43, 44, extending parallel with the plane PL out from the periphery of the base member 30. The flanges 40 are formed integrally with the base member 30 but can be formed separately and connected thereto. A plurality of grip members 50 are arranged on the base member 30 via the flanges 40. In the shown embodiment, each flange member 41, 42, 43, 44 comprises two grip members 51, 52, 53, 54 (not all grip members are shown). The grip members 51, 52, 53, 54 are flexible and will deform somewhat as the they are connected to the vial 2, to thereafter return substantially to their original position after passing a flange on the vial 2, whereafter the grip members connect the medical device connector 1 to the vial 2 in a known "snap-on" manner.

FIG. 2*a* shows a view towards the second flange 42 and the two grip members 53, 54 of the second flange 42. Each grip member 50 of the medical device connector 1 comprises a proximal end P and a distal end D, in FIG. 2*a* this is illustrated by the grip member 53 having a proximal end $\mathbf{53}_P$ and a distal end $\mathbf{53}_D$. The proximal ends are nearer to the base member 30.

Between each adjacent grip member 52, 53 of separate flanges 41, 42, four bridge sections 60 are provided. As is noticed, the bridge sections extend from the distal ends of the grip members and thereby connect the distal ends $\mathbf{52}_D$, $\mathbf{53}_D$ of the grip members 52, 53 of separate flanges 41, 42. Each bridge section 60 comprises a wedge portion 61 enabling a snap on function to the vial 1 shown in FIG. 1.

Figure 2D:
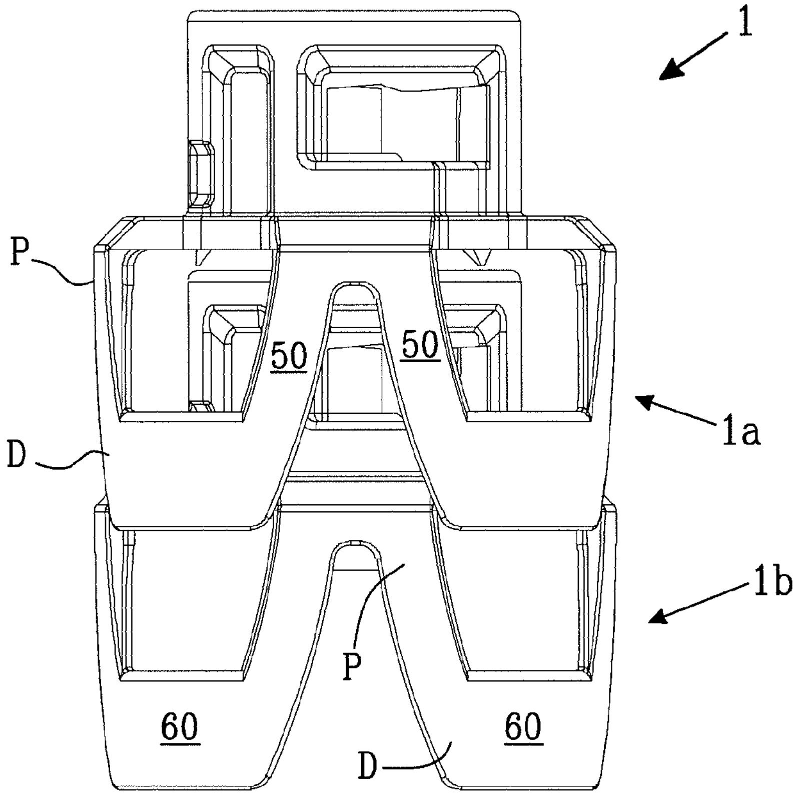
FIG. 2*d* shows two medical device connectors, as shown in FIG. 1, piled in a stack of medical device connectors.

The distance between the proximal ends is smaller than the distance between the distal ends of the grip members. This provides for grip members having a somewhat tilted appearance and extending in a non parallel direction with respect to the centre axis A. This enables a plurality of medical device connectors 1*a*, 1*b* to be stacked in a relatively compact manner, as shown in FIG. 2*d*.

Figure 3:
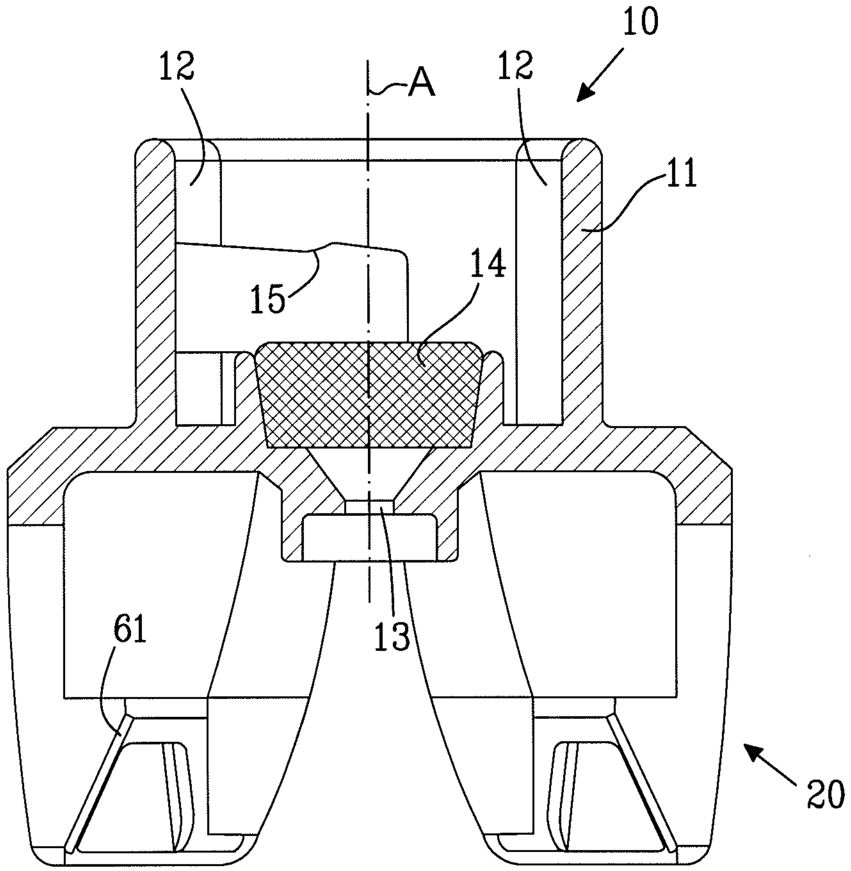
FIG. 3 shows a cross section of the medical device connector shown in FIG. 1.

FIG. 3 shows a cross section of the medical device connector 1, shown in FIG. 1, and 2*a*-2*d*. The first connection site 10 comprises a neck element 11 having two guiding tracks 12 (both shown in e.g. FIG. 2*c*) for receiving lock protrusions 4 of the piercing device 3, shown in FIG. 1. Each guiding track 12 comprises a locking edge 15. The lock protrusions 4 of the piercing device 3 cooperate with the locking edge 15 to connect the piercing device 3.

Intersecting with the centre axis A is a through going aperture 13 arranged to permit a needle of the piercing device 3 to extend therethrough after assembly and during use. A barrier member 14 made from e.g. silicone rubber material or a thermoplastic elastomer (TPE) is arranged to seal around such needle during use and to seal after use. The barrier member 14 covers the through going aperture.

Turning back to FIG. 1 again, the neck element 11 comprises two opposing guiding tracks 12, symmetrically positioned. The guiding tracks 12 exhibit an L-form, comprising a first vertical section 80 and a substantially horizontal section 81 arranged substantially perpendicular to the vertical section 80.

Figure 4A:
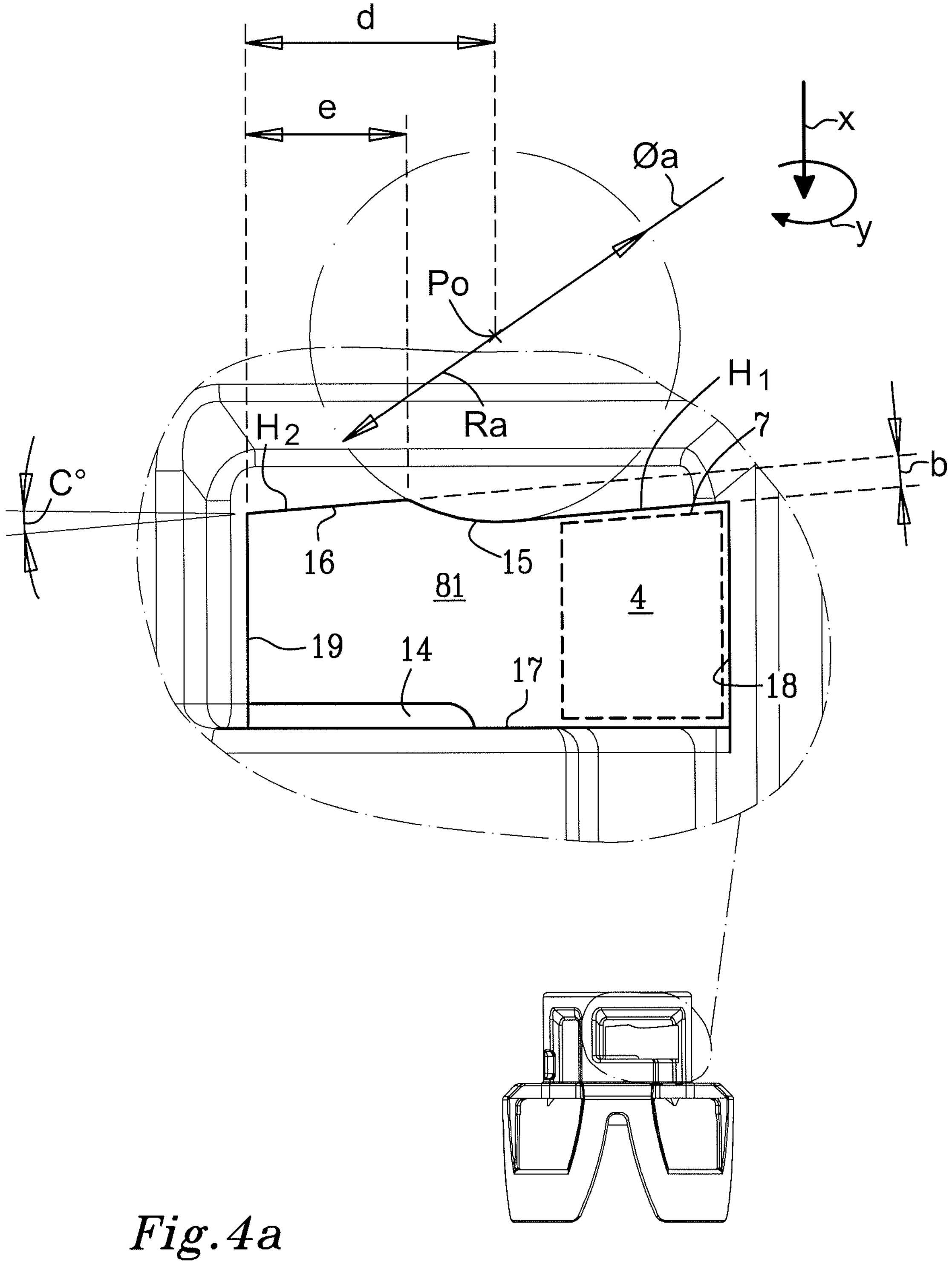
FIG. 4*a*-4*b* shows parts of the guiding track of the medical device connector as shown in FIG. 1 in a more detailed view.
Figure 4B:
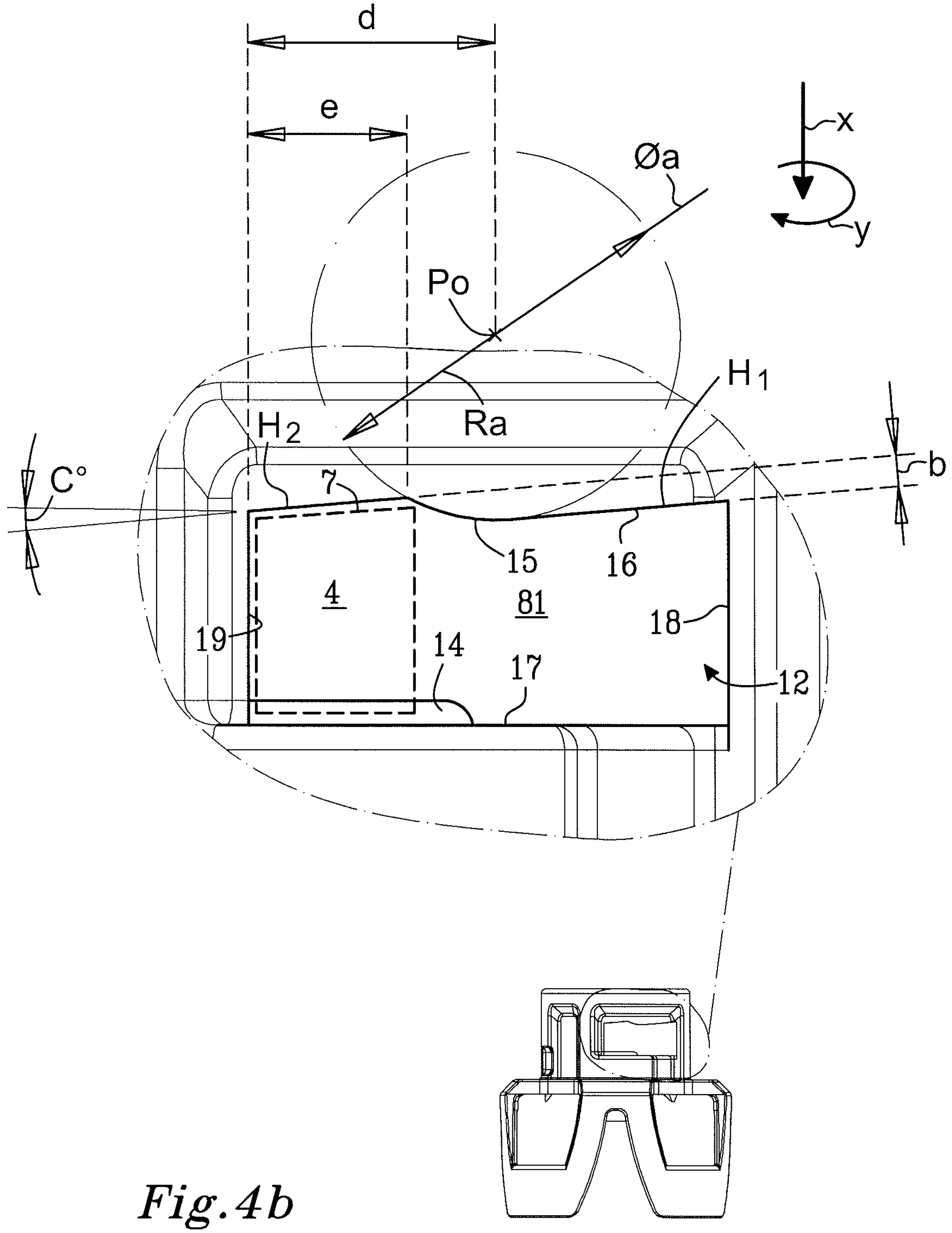

FIGS. 4*a*-4*b* show an enlargement of parts of the neck element 11 and one of the guiding tracks 12 of the first connection site 10 of the medical device connector 1 seen in FIGS. 1-4. The guiding track 12 comprises the locking edge 15, or barrier section, which the lock protrusions 4 of the piercing device 3 are intended to cooperate with during assembly, as illustrated in FIG. 1. The tip 5 of the piercing device 3, with its barrier member 6 and lock protrusions 4, as shown in FIG. 1, is inserted into the neck element 11 of the first connection site 10. During the insertion, the lock protrusions 4 of the piercing device 3 slide in the vertical section 81 of the guiding track 12.

The arrows X, Y, shown in FIGS. 1 and 4*a*-4*b*, show how the piercing device 3 is moved during insertion and locking, and in which order; X before Y. Disengagement is done in the opposite order and direction. First, with a vertical motion illustrated by arrow X, the tip 4 of the piercing device 3 is inserted so that the barrier member 6 of the piercing device 3 is positioned directly adjacent the barrier member 14 of the medical device connector 1, shown in FIG. 3. The barrier members 6, 14 are compressed by the vertical movement. When the lock protrusions 4 of the piercing device 3 are aligned with the vertical sections 81 of the guiding tracks 12, the piercing device 3 can be turned clockwise, as indicated by the arrow Y. During the clockwise turning, which in an embodiment of course can be counter clockwise should the guiding track 12 extend in that direction, the lock protrusion 4 is forced into the locked position. As is noticed, the neck element 11 comprises two guiding tracks 12 and the piercing device 3 comprises two lock protrusions 4, although each feature might be described in the singular. As the piercing member 3 is in the locked position, the needle can be exposed, penetrate the barrier members 6, 14, to provide for drug delivery or drug administration.

In FIG. 4*a*, parts of the lock protrusion 4 of the piercing device 3 are indicated with a dotted line and shown at the position before the turning motion, or the locking motion, i.e. before the motion indicated by arrow Y is performed. FIGS. 4*a*-4*b* also show the horizontal section 81 of the guiding track 12. As is noticed in FIG. 4*a*, the locking edge 15 smoothly extends in a smooth curvature between a first and a second level H1, H2, illustrated with the distance b in FIG. 4*a*-4*b*. The distance b can be 0.2-3 mm, preferably 0.2-1 mm. The locking edge 15 extends as a smooth curvature, the curvature of which is a function of a radius Ra, indicated by the diameter Øa. The radius Ra, being half of the diameter Øa. The radius Ra can be between 1-10 mm, preferably between 2-8 mm even more preferably between 3-5 mm. In the shown embodiment in FIG. 4*a*, the radius a is about 3 mm. The locking edge thus enables a good connection between the piercing device 3 and the medical device connector 1 which is easy to lock and unlock while still permitting a user to easily turn the piercing device 3 to a locked position, from the position indicated in FIG. 4*a* with the dotted lines of the lock protrusion 4. In an embodiment, the locking edge 15 can be extending in a smooth curvature, the curvature of which is the function of two radii, different or the same, but with different points of origin. The locking edge 15 thus extends smoothly between the two levels. By smoothly is meant a substantially continuous transition with no sharp edges.

The horizontal section 81 of the guiding tracks 12 comprises a distal surface 16, a proximal surface 17, a first and a second vertical surface 18, 19, the distal surface 16 being further away from the base member 30, than the proximal surface 17. The locking edge 15 has a radius curvature, illustrated by arrow Ra in FIGS. 4*a* and 4*b*. The radius Ra has a point of origin $P_O$ at a distance d from the second side 19 of the horizontal section 81 of the guiding track 12, and starts at a distance e from the second side 19 of the horizontal section 81 of the guiding track 12. The distance d can be between 3-20 mm. The distance e can be between 1-6 mm, preferably between 2-5 mm. In the shown embodiment the distance e is about 2.6 mm. It should be noted that the distance d should be adapted after the radius Ra, distance e and the distance b.

The distal surface 16 of the guiding tracks 12 is further arranged with an angle c, as indicated in FIG. 4*a*-4*b* with respect to a proximal surface 17 of the guiding tracks 12. The proximal surface 17 of the guiding tracks 12 can be considered to be horizontal, or parallel with a still water line. The angle c is advantageously 0-15°, preferably 2-10°, even more preferably 5-7°. In the shown embodiment the angle c is 5°. FIGS. 4*a*-4*b* also show parts of the barrier member 14. The angled surface enables the piercing device 3 to be compressed towards the medical device connector 1 during assembly and the clockwise turning of the piercing device 3, as indicated by arrow Y in FIG. 4*a* as the lock protrusion 4 is moved towards the locking edge 15. The piercing device 3 is subjected to a counter force imparted by the compressed barrier member 14 and the compressed barrier member 6 of the piercing device 3 if such is present. The counter force exerts an upwardly directed force component on the piercing device 3 in a direction opposite to the arrow X.

As the lock protrusion 4 passes the locking edge 15, the upward force component forces a distal surface 7 of the lock protrusion 4 against the distal surface 16 of the guiding track 12 and thus keeps it in a locked position. FIG. 4*b* shows the lock protrusion 4 in the locked position. Although referred to as the locked position, it is only locked form movement along the vertical arrow X.

The smooth curvature of the locking edge 15 enables a user to smoothly unlock, or more accurately, to smoothly pass the lock protrusion across the raised barrier which the locking edge 15 is composed of; thus enabling the unlocking of the piercing device from the first connection site of the medical device connector 1 to be performed simply, yet providing an effective locking function.

Figure 5:
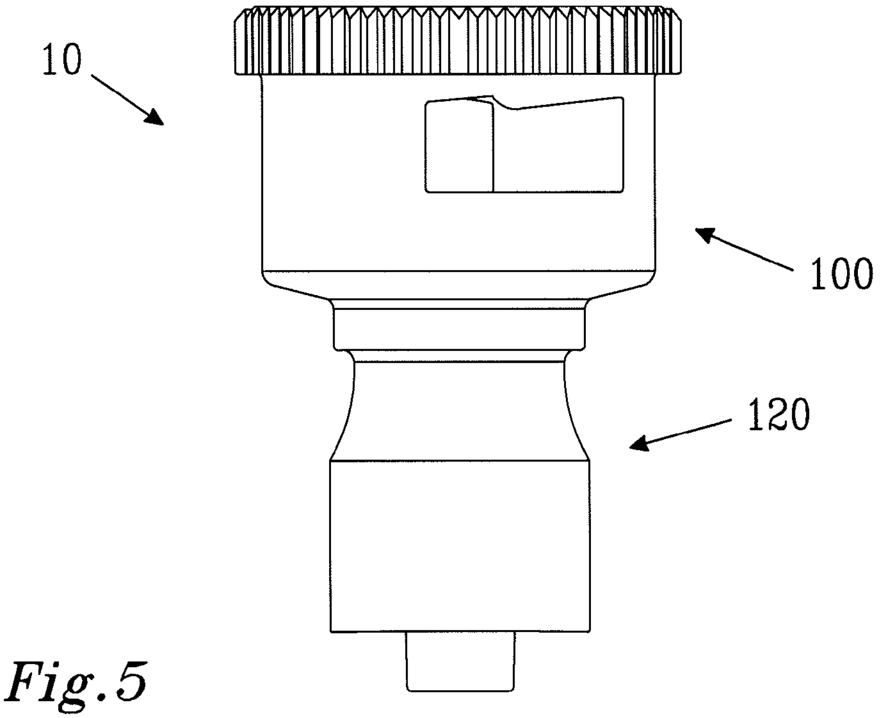
FIGS. 5-6 show an alternative medical device having a first connection site, identical to the medical device connector shown in FIG. 1.
Figure 6:
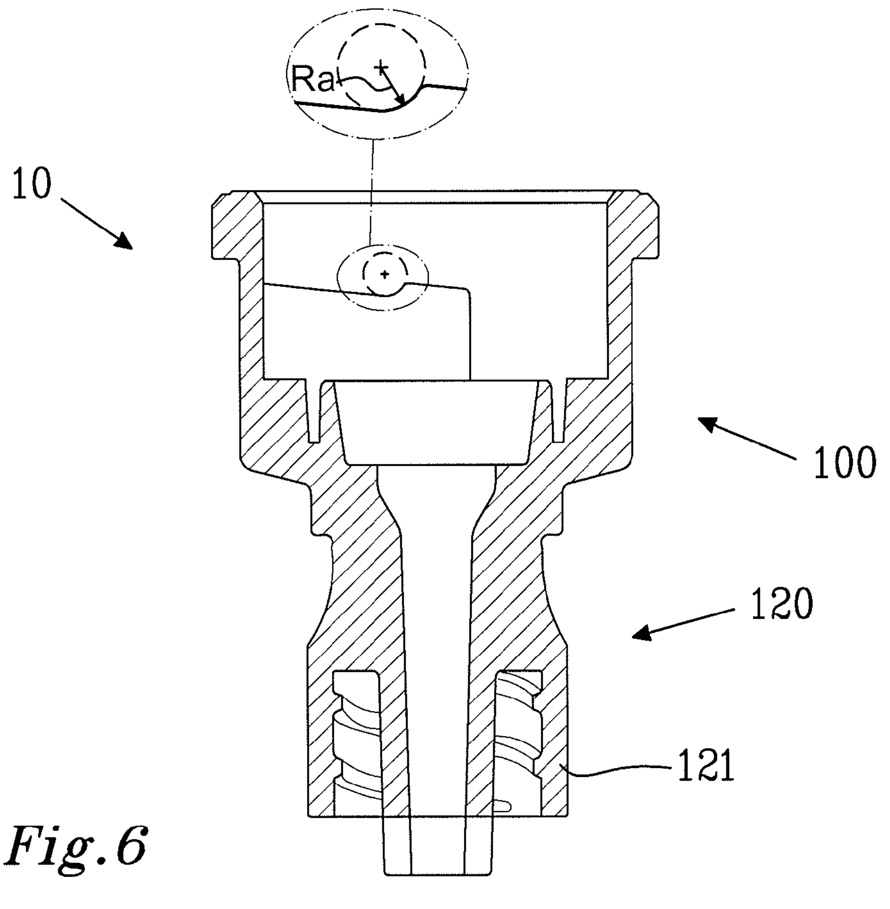

The present invention can be applied on a plurality of medical device connectors. FIGS. 5-6 show an alternative embodiment of a medical device connector 100 comprising a first and a second connection site 10, 120. The first connection site being the same first connection site 10 as described above. The second connection site 120 is a traditional male luer lock coupling 121. It should be noted that the second connection site could be a female luer lock coupling.

Figure 7:
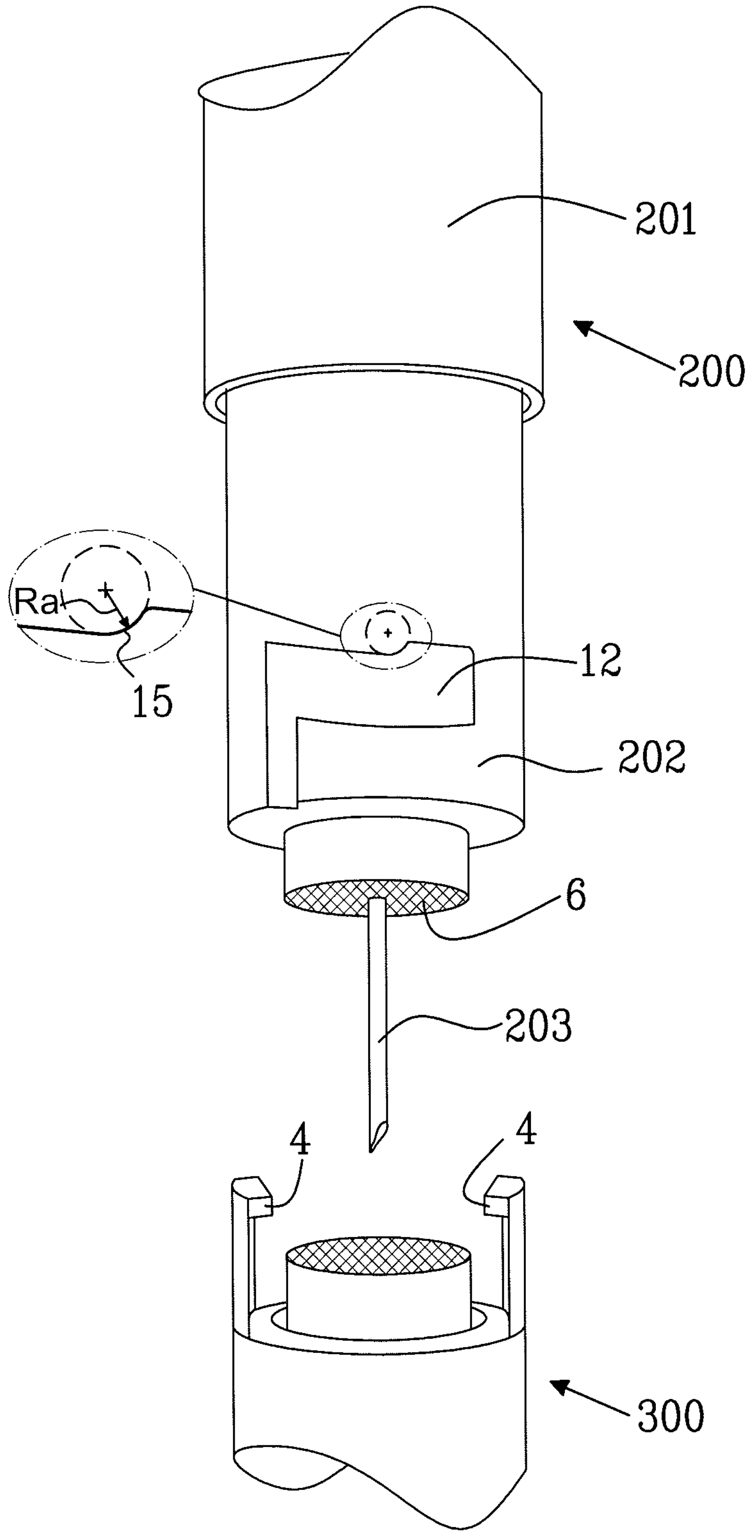
FIG. 7 shows an alternative medical device in the form of a piercing member protection device.

FIG. 7 shows an alternative embodiment of the present invention. The guiding track 12, as described above, is in this embodiment arranged on a piercing member protection device 200. The piercing member protection device comprises a first and a second sleeve member 201, 202 and a piercing member 203. The first and a second sleeve members 201, 202 are telescopically arranged to each other such that when said first sleeve member 201 is in a first position, the piercing member 203 is not exposed, and when the first sleeve member 201 is in a second position, the piercing member 203 is exposed. In FIG. 7, the piercing member 203 is exposed and the first sleeve 201 is in its second position, with respect to the second sleeve 202. It should be noted that the second position, as seen in FIG. 7, with the piercing member 203 exposed is in practice only present after connection with the second medical device 300 and a full connection has been achieved.

The sleeve member 202 comprises at least one guiding track 12, preferably two guiding tracks 12. The guiding tracks 12 are arranged symmetrically on the side of eth sleeve 202 and are formed in the sleeve 202.

The barrier member 6 of the piercing member 200, and the barrier member 14 of the medical device connector 1, is arranged to cooperate with the said lock protrusions 4 of said second medical device 3, 300 so as to exert a force component to said second medical device. The force component helps to keep the lock protrusion in a locked position when the medical device has been connected to the second medical device. The medical device can be a piercing member free medical device, i.e. a medical device for e.g. transferring fluid between two vials without the use of e.g. a needle.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A medical device comprising a first connection site for connecting a second medical device, said first connection site comprising;

at least one guiding track for guiding a lock protrusion on said second medical device, said at least one guiding track being arranged with a surface comprising a locking edge, said locking edge being arranged to cooperate with said lock protrusion on said second medical device, said locking edge extending between a first and a second level (H1, H2), wherein said locking edge having a smooth curvature between said first and said second level (H1, H2), the curvature of which is a function of at least one radius (Ra).

2. The medical device according to claim 1, wherein said radius (Ra) is between 1-10 mm.

3. The medical device according to claim 1 or 2, wherein said distance (b) between said first and said second level (H1, H2) is 0.2-3.0 mm.

4. The medical device according to claim 1, wherein said locking edge extends in a smooth curve between said first and said second level (H1, H2), and said curvature is a function of two radii.

5. The medical device according to claim 1, wherein said guiding track comprises at least a horizontal section said horizontal section, comprising a distal and proximal surface, and a first and a second vertical surface.

6. The medical device according to claim 5, wherein said radius (Ra) has a centre of origin ($P_O$) positioned at a distance (d) from said second vertical surface of said horizontal section of said guiding track.

7. The medical device according to claim 1, further comprising a neck element that extends from a base member for receiving a part of said second medical device into said neck element, said neck element comprising said at least one guiding track.

8. The medical device according to claim 7, wherein said neck element is a cylinder neck element.

9. The medical device according to 5, wherein said guiding track comprises a vertical section arranged substantially perpendicular to said horizontal section, said vertical section arranged to initially receive said lock protrusion during assembly.

10. The medical device according to claim 1, wherein said medical device is a piercing member protection device and said guiding track is arranged on said piercing member protection device.

11. The medical device according to claim 10, wherein said piercing member protection device comprises a sleeve member and said at least one guiding track is formed in said sleeve member.

12. The medical device according to claim 1, wherein said medical device comprises a second connection site for connecting an additional medical device.

13. The medical device according to claim 1, wherein said medical device comprises a barrier member, in that said barrier member arranged to cooperate with said lock protrusion of said second medical device so as to exert a force component to said second medical device.

14. The medical device according to claim 1, wherein said medical device is a piercing member free medical device.

15. The medical device according to claim 1, wherein said distance (b) between said first and said second level (H1, H2) is 0.2-1.0 mm.

16. The medical device according to claim 2, wherein said distance (b) between said first and said second level (H1, H2) is 0.2-1.0 mm.

* * * * *